United States Patent
Zhang et al.

(10) Patent No.: US 6,207,138 B1
(45) Date of Patent: Mar. 27, 2001

(54) FLUORIDE FREE DENTAL REMINERALIZATION

(75) Inventors: Yun Po Zhang, Hillsborough; Abdul Gaffar, Princeton, both of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/372,355

(22) Filed: Aug. 11, 1999

Related U.S. Application Data

(63) Continuation of application No. 08/858,638, filed on May 19, 1997.

(51) Int. Cl.[7] .............................. A61K 7/16; A61K 7/22
(52) U.S. Cl. ................................................. 424/49; 424/54
(58) Field of Search ........................................ 424/49–88

(56) References Cited

U.S. PATENT DOCUMENTS

| | | | |
|---|---|---|---|
| 4,992,420 | * | 2/1991 | Neeser . |
| 4,994,441 | * | 2/1991 | Nesser . |
| 5,015,628 | * | 5/1991 | Reynolds et al. . |
| 5,075,424 | * | 12/1991 | Tanimoto et al. . |
| 5,089,255 | * | 2/1992 | Gaffar . |
| 5,130,123 | * | 7/1992 | McDougel et al. . |
| 5,227,154 | * | 7/1993 | Reynolds . |
| 5,278,288 | * | 1/1994 | Kawasaki et al. . |
| 5,279,814 | * | 1/1994 | Wulkins . |
| 5,280,107 | * | 1/1994 | Kawasaki et al. . |
| 5,427,769 | * | 6/1995 | Behringer . |
| 5,531,982 | * | 7/1996 | Gaffar . |
| 5,536,526 | * | 7/1996 | Virtanen . |
| 5,605,677 | * | 2/1997 | Schumann . |
| 5,616,361 | * | 4/1997 | Virtanen . |
| 5,741,773 | * | 4/1998 | Zhang et al. ............................ 424/49 |
| 5,834,427 | * | 11/1998 | Hancock . |
| 5,853,704 | * | 12/1998 | Zhang et al. ............................ 424/52 |
| 5,981,475 | * | 11/1999 | Reynolds ................................ 514/6 |

* cited by examiner

Primary Examiner—Shep K. Rose
(74) Attorney, Agent, or Firm—Paul Shapiro

(57) ABSTRACT

A method and composition for remineralizing teeth wherein the composition contains a mixture of a casein glycomacropeptide and xylitol.

4 Claims, No Drawings

FLUORIDE FREE DENTAL REMINERALIZATION

This is a continuation of pending prior art application Ser. No. 08/858,638 filed May 19, 1997 which application is now pending and is incorporated herein by reference.

BACKGROUND OF THE INVENTION

1. Field of the Invention

The present invention relates to oral compositions in the form of dentifrices and mouthwashes providing improved remineralization effects.

2. The Prior Art

In the mouth, there is a natural equilibrium between hydroxyapatite being dissolved from the enamel of teeth, on the one hand, and hydroxyapatite being formed on or in the teeth from substances occurring naturally in the saliva, on the other. The equilibrium is such that hydroxyapatite is dissolved, a cariogenic condition arises which is referred to as demineralization. If the equilibrium is such that hydroxyapatite is being formed in demineralized enamel, this is referred to as remineralization. By remineralization, pre-existing tooth decay and caries can be reduced or eliminated by natural means.

It has long been known that fluoride-providing compounds, even in low concentrations, are a safe and effective route for the promotion of the remineralization process. Although effective, excess amounts of fluoride releasing compounds have produced cosmetically objectionable fluorosis (mottling) in developing teeth in geographic areas in which the water supply contains relatively high levels of fluoride compounds.

Xylitol in combination with fluoride releasing compounds is known for the treatment of dental structures to provide prophylactic prevention of carious conditions, and/or remineralization of pre-existing carious conditions for example U.S. Pat. No. 5,089,255. EP Publication No. 0138705, discloses anticaries compositions containing xylitol and mixtures of at least two fluoride salts providing 2,000–20,000 ppm fluoride ion. EP Publication No. 0251146 discloses an oral composition having a dental plaque preventing activity containing a mixture of xylitol, a fluoride releasing compound, and one zinc ion releasing compound Xylitol alone, even at concentration levels of 10% by weight in the absence of fluoride releasing compounds, does not provide a remineralization effect comparable to that provided by fluoride releasing compounds. when incorporated in oral compositions.

Therefore there is a need in the art for a xylitol based oral composition, which is substantially free of fluoride ion releasing compounds which provides a remineralization effect comparable to that observed when used in combination with fluoride ion releasing compounds.

SUMMARY OF THE INVENTION

In accordance with the present invention there is provided a substantially fluoride-free composition and method of remineralizing demineralized portions of tooth structures which comprises applying to such portions an oral composition in the form of a dentifrice or mouthwash containing about 1.0 to about 20% by weight xylitol and about 10 to about 20% by weight of a casein glycomacropeptide.

In the practice of the present invention, the defined combination of xylitol and casein glycomacropeptide employed in amounts within the indicated ranges to achieve optimum remineralization effects, have unexpectedly been found to coact synergistically to yield remineralization results equal to or greater than those obtainable when xylitol and fluoride ion-releasing compounds are used in combination.

DESCRIPTION OF THE PREFERRED EMBODIMENTS

In the practice of the present invention, xylitol is present in the oral composition at a concentration of about 1 to about 20% by weight, preferably about 5 to about 15% by weight and most preferably about 7 to about 12% by weight.

Casein glycomacropeptide compounds useful in the practice of the present invention are known to the art to be effective antibacterial agents against microorganisms responsible for dental plaque and caries. For example, U.S. Pat. Nos. 4,992,420 and 4,994,441 disclose that casein phosphopeptides derived from kappa-casein are effective for inhibiting the growth of streptococcus mutans, a bacteria species associated with dental caries and plaque formation.

The term "kappa-caseino glycopeptides" includes within its meaning a caseino glycopeptide, which is the water soluble component emanating from the hydrolysis of kappa-casein by rennet, and a caseino-glycopeptide obtained by proteolysis of caseino-macroglycopeptide. Desialylated derivatives are obtained from caseino glycopeptides by more or less complete elimination of the sialic acids, i.e., N-acetylneuraminic and N-glycollylneuraminic acids, from the oligosaccharide chains of the caseino glycopeptide. The preparation of kappa-caseino-glycopeptides is disclosed in U.S. Pat. No. 4,992,420. Other casein glycomacropeptide compounds useful in the practice of the present invention are the kappa-caseino glycomacropeptides disclosed in U.S. Pat. No. 5,075,424.

The casein glycomacropeptide is incorporated in the oral composition of the present invention at a concentration of at least about 10% by weight, and preferably at about 10 to about 20% by weight.

In the preparation of oral compositions utilizing casein glycomacropeptides it has been previously determined that these compounds are not compatible with anionic surfactants such as sodium lauryl sulfate conventionally used to prepare dentifrice compositions such as toothpastes and gels, the casein glycomacropeptide being biologically inactivated by the surfactant.

To avoid the biological inactivation of the casein glycomacropeptide, a hydrolyzed protein compound is incorporated in the oral composition of the present invention, as disclosed in copending patent application Ser. No. 08/639,871 filed Apr. 26, 1996.

Hydrolyzed protein compounds useful to preserve the biological activity of the casein glycomacropeptides include hydrolyzed collagen proteins, specifically positively charged hydrolyzates containing high concentrations of basic amino acids obtained by extraction from a partially hydrolyzed collagen faction and isolation by ion exchange treatment with an anion exchange resin or a partially charged hydrolyzed collagen protein. Such hydrolyzed collagen proteins are known to the art and are more fully described in U.S. Pat. No. 4,391,798. Commercially available hydrolyzed collagen proteins include Crotein Q®, a quaternary derivative of hydrolyzed collagen protein available commercially from Croda Inc., New York, N.Y. Crotein Q has a minimum pH of 9.5–10.5, is an off-white, free flowing powder and its adopted name is steartrimonium hydrolyzed animal protein. Another example of a commercially available hydrolyzed collagen protein is gelatin (food grade) available from American Gelatin Company, a hydrolyzed collagen protein prepared by boiling animal parts such as skin, tendons, ligaments and bones with water.

The presence of about 0.1 to about 2.5% by weight of the hydrolyzed protein compound in the oral composition of the present invention is sufficient to inhibit any biological inactivation of the casein glycomacropeptide caused by the concurrent presence of an anionic surfactant in the composition.

To prepare a dentifrice composition such as a toothpaste or gel, abrasives including conventional dentifrice abrasives, such as finely divided silica, hydrated alumina, calcined alumina, calcium carbonate, sodium bicarbonate and dicalcium phosphate (anhydrous and/or dihydrate) are incorporated in a vehicle at a concentration of about 10 to about 30% by weight based on the composition and preferably at a concentration of about 15 to about 25% by weight. At these abrasive levels, the vehicle is comprised of about 25 to about 40% by weight water as well as a humectant such as glycerol, sorbitol, propylene glycol or mixtures thereof at a concentration of about 25 to about 45% by weight and preferably about 25 to about 35% by weight of the composition.

Thickeners or gelling agents are used in the preparation of the dentifrices of the present invention and include silica thickeners, carboxymethyl cellulose, sodium carboxymethyl cellulose, carob bean gum, iota carrageenan, gum tragacanth, hydroxymethyl cellulose, hydroxyethyl cellulose, hydroxypropyl cellulose, and alginates and are incorporated in the oral compositions at concentrations from about 0.2 to about 3.0% by weight.

Surfactants which may be included in the composition of the present invention include anionic surfactants such as the water soluble salts of the higher alkyl sulfates or sulfoacetate, such as sodium lauryl sulfate, sodium lauryl sulfoacetate or other suitable alkyl sulfates or sulfoacetates having 8 to 18 carbon atoms in the alkyl group; water soluble salts of sulfonated monoglycerides of higher fatty acids, such as sodium coconut monoglyceride sulfonate or other suitable sulfonated monoglyceride of a fatty acid of 10 to 18 carbon atoms; sodium lauryl phosphate salts of amides of higher fatty acid, e.g., 12 to 16 carbon atom acids, with lower aliphatic amino acids, e.g., taurine or sarcosine, or other amino acid of 2 to 6 carbon atoms, such as sodium-N-methyl-N-palmitoyl tauride, sodium N-lauroyl-, N-myristoyl- and N-palmitoyl sarcosinates; water soluble salts of the esters of such fatty acids with isethionic acid or with glycerol monosulfate, such as the sodium salt of monosulfated monoglyceride of hydrogenated coconut oil fatty acids; water soluble salts of olefin sulfonates, e.g., alkene sulfonates or hydroxyalkene sulfonates or mixtures thereof having 12 to 16 carbon atoms in the carbon chain of the molecule; and water soluble soaps of higher fatty acids, such as those of 12 to 18 carbon atoms, e.g., coconut fatty acids.

Surfactants are included in the composition of the present invention at a concentration of about 0.5 to about 3.0% by weight and preferably about 1.0 to about 2.5% weight.

Various other materials may be incorporated into the dentifrice preparations of the present invention such as flavoring agents, sweetening agents and coloring materials such as dyes and pigments which are incorporated in the dentifrice compositions of the present invention in amounts which do not adversely affect the properties and characteristics desired in the dentifrice components. Examples of suitable flavoring constituents include flavoring oils, for example, oils of spearmint, peppermint, wintergreen, sassafras, clove, sage, as well as methyl salicylate. Examples of sweetening agents include lactose, maltose, sodium cyclamate and saccharine. Suitably, flavor and sweetening agents together comprise from about 0.01 to 5% or more of the composition. Preferably, the amount of flavoring oil is about 0.5 to about 2.0% by weight and the sweetening agent is from 0.1 to 4 or 0.1 to 0.5% by weight (the latter range being for artificial sweeteners, such as saccharine).

Pigments such as $TiO_2$ and coloring materials which are generally commercially available food dye solutions which are inert with respect to the other ingredients of the oral composition are included at a concentration of about 0.05 to about 2.0% by weight.

In the preparation of dentifrices such as toothpastes and gels, a premix in water is formed in which the water soluble ingredients are first dissolved followed by the water insoluble ingredients, if any. If desired, the lipophilic components may be premixed together and such premix can be mixed with the hydrophiles premix, after which the water insoluble particulate materials may then be blended. The pH of the dentifrice is maintained at a neutral pH and preferably a pH of between 6.7 and 7.2. For example, the thickener is dispersed with water and humectants. The surfactant, hydrolyzed protein compound, casein glycomacropeptide, abrasive, sweetener, flavor and colorant are then separately added and uniformly dispersed. The dentifrice is then thoroughly deaerated (e.g., in vacuo) and packaged. The addition and mixing of the ingredients is conducted in a low humidity environment and preferably under a vacuum of 20–30 inches and preferably 28–30 inches mercury.

In addition to dentifrices such as toothpaste or gel compositions for oral application containing xylitol and casein glycomacropeptide, the oral composition of the present invention may be in any other convenient form, such as a mouthrinse, tooth powder or chewing gum.

A typical mouthrinse prepared in accordance with the practice of the present invention contains the following ingredients in percent by weight based on the weight of the mouthrinse composition.

| Ingredients | Wt. % |
|---|---|
| Ethanol (90%) | 5–10 |
| Glycerin | 10–20 |
| Xylitol | 1–20 |
| Casein Glycomacropeptide | 10–20 |
| Sodium Lauryl Sulfate (SLS) | 0.1–2.5 |
| Gelatin | 0.1–2.5 |
| Flavor | 0.2–1.5 |
| Sodium Saccharin | 0–5 |
| Sodium Benzoate | 0–5 |
| Water | Q.S. |

A typical toothpowder prepared in accordance with the practice of the present invention contains the following ingredients in percent by weight based on the weight of the toothpowder composition.

| Ingredients | Wt. % |
|---|---|
| Hydrated Alumina | 70–80 |
| Glycerin | 10 |

-continued

| Ingredients | Wt. % |
|---|---|
| SLS | 0.1–2.5 |
| Sodium Saccharin | 0.1 |
| Flavor | 1.0 |
| Xylitol | 1–20 |
| Gelatin | 10–20 |
| Hydrolyzed Protein Stabilizer | 0.1–2.5 |
| Water | Q.S. |

A typical chewing gum formula contains the following ingredients, in percent by weight, based on the weight of the total formulation:

| Ingredients | % by Weight |
|---|---|
| Gum Base (Natural or synthetic elastamer filler, e.g. gum arabic sorbitol) | 75–85 |
| Xylitol | 1–20 |
| Casein Glycomacropeptide | 10–20 |
| Gelatin | 0.1–2.5 |
| SLS | 0.1–2.5 |
| Dextrose | 0.2–2 |

The following example serves to provide further appreciation of the invention but is not meant in any way to restrict the effective scope of the invention. All percentages throughout the specification and claims are by weight % of the final composition unless otherwise indicated and wherein all percentages will total 100% of ingredients in the final composition.

EXAMPLE

To determine the remineralization effect on teeth of a combination of xylitol and a kappa-caseino glycomacropeptide when present in a toothpaste composition, a composition designated Toothpaste 1, containing these ingredients was prepared by adding thickeners to a pre-mix of water and humectant at a slightly elevated temperature (e.g., from 35 to 60° C.) with proportioning the ingredients to a creamy or gel consistency. Additional ingredients were then added. The toothpastes were adjusted to a pH of 6.7 with NaOH. The resultant toothpaste was then deaerated, flavor was introduced and the toothpaste was packed in tubes. The ingredients of Toothpaste 1 are listed in Table I below. For purposes of comparison, the procedure of Example 1 was repeated except the concentration of the KCGMP in the toothpaste was less than 10% by weight, designated Toothpaste 2, or xylitol or KCGMP was not included in the toothpaste composition such compositions being designated Toothpastes 3 and Toothpaste 4 respectively. The ingredients of Toothpastes 2, 3 and 4 are also listed in Table I below.

TABLE I

| Ingredients | Toothpaste 1 Weight (%) | Toothpaste 2 Weight (%) | Toothpaste 3 Weight (%) | Toothpaste 4 Weight (%) |
|---|---|---|---|---|
| Glycerin | 12.800 | 14.000 | 20.000 | 20.000 |
| Carboxymethyl Cellulose | 0.200 | 0.200 | 0.200 | 0.300 |
| Iota Carrageenan | 0.650 | 0.650 | 0.650 | 0.800 |
| Deionized Water | 44.590 | 48.450 | 47.140 | 48.450 |
| Kappa-Casein Glyco-macropeptide (CGMP) | 10.000 | 5.000 | 10.000 | — |
| Xylitol | 10.000- | 10.000 | — | 10.000 |
| Sodium Saccharin | — | — | 0.250 | — |
| Sodium Benzoate | 0.300 | 0.300 | 0.300 | 0.300 |
| Silica Abrasive (Zeo-115) | 18.000 | 18.00 | 18.000 | 18.000 |
| Sodium Lauryl Sulfate | 1.000 | 1.000 | 1.000 | 1.000 |
| Gelatin Stabilizer | 1.000 | 1.000 | 1.000 | — |
| Titanium Dioxide | 0.400 | 0.400 | 0.400 | 0.400 |
| Flavor | 0.750 | 0.750 | 0.750 | 0.750 |
| NaOH (50%) | 0.310 | 0.250 | 0.310 | — |
| Total | 100.00 | 100.00 | 100.00 | 100.00 |

The toothpaste composition of the present invention (Toothpaste 1) as well as comparative Toothpastes 2, 3 and 4 were evaluated in vivo for remineralization efficacy using the surface microhardness methodology described in Zhang et al, J. Clini. Dent. 6:148–153 (1995). As a placebo, a silica toothpaste containing no fluoride was used as a negative control (designated Toothpaste 5) and a commercially available fluoride toothpaste containing 1100 ppm NaF bearing the indication by the Council on Dental Therapeutics of the American Dental Association as being effective in preventing caries, was used in the study as a positive control (designated Toothpaste 6).

The method of assessing enamel remineralization via surface microhardness was performed in a randomized, crossover, double-blind, intra-oral remineralization study conducted with 12 healthy adults. Enamel demineralization was achieved in vitro by covering bovine enamel blocks with exogenous oral bacteria, S. Mutans 1600 Ingbritt, containing glucan which was then exposed to sucrose. In the intra-oral treatment phase, subjects were fitted with oral maxillary palatal retainers, each holding four demineralized enamel blocks. Subjects brushed their teeth for 30 seconds with 1.5 grams of a test dentifrice, swished for an additional 60 seconds, rinsed with water and then retained the blocks intra-orally for 4 hours. Percent mineral recovery for each enamel block was calculated as the ratio of the changes in enamel microhardness due to treatment (remin) and sucrose challenge (demin). The washout period between test toothpastes was one week. The subjects were required to use a silica placebo toothpaste as a normal daily hygiene during the whole study.

The results of the study are recorded in Table II below.

TABLE II

| Toothpaste No. | Remin. (% Mineral Recovery) |
|---|---|
| 1. 10% CGMP/10% Xylitol | 45.78 ± 17.04 |
| 2. 5% CGMP/10% Xylitol | 38.07 ± 11.26 |
| 3. 10% CGMP | 37.01 ± 16.04 |
| 4. 10% Xylitol | 13.33 ± 4.23 |
| 5. Placebo (Silica abrasive, no F−) | 0.38 ± 4.68 |
| 6. Commercial Fluoride Toothpaste (1100 ppm F as NaF) | 33.52 ± 11.77 |

As shown in the attached Table II, remineralization (% mineral recovery) of the placebo toothpaste (Toothpaste 5), the 10% Xylitol toothpaste (Toothpaste 4) the commercial fluoride toothpaste (Toothpaste 6), the 10% CGMP toothpaste (Toothpaste 3), the 5% CGMP/10% Xylitol toothpaste (Toothpaste 2), and the toothpaste of the present invention 10% CGMP/10% Xylitol toothpaste (Toothpaste 1) was 0.38%, 13.33%, 33.52%, 37.01%, 38.07% and 45.78% respectively. Statistical analysis (ANOVA) showed that (1) remineralization efficacy of the commercial fluoride toothpaste, the 10% CGMP toothpaste, the 5% CGMP/10% Xylitol toothpaste and the 10% CGMP/10% Xylitol toothpaste were significantly better than the placebo toothpaste and the 10% Xylitol toothpaste; (2) the 10% CGMP toothpaste and the 5% CGMP/10% Xylitol toothpaste provided the same remineralization effect as the commercial fluoride toothpaste; and (3) the 10% CGMP/10% Xylitol toothpaste of the present invention promoted statistically significant better remineralization than a clinically proven commercial fluoride toothpaste (Toothpaste 6).

What is claimed is:

1. A method of renmineralizing demineralized portions of tooth structures comprising preparing an oral composition containing an aqueous vehicle about 10 to about 20% by weight of a casein glycomacropeptide and about 1 to about 20% by weight of xylitol, applying the oral composition to demineralized portions of tooth structures whereby such application provides substantially better retnineralizing effect in the absence of the presence of a fluoride, providing compound than that provided by the individually employed xylitol and casein glycomacropeptide compounds.

2. The method according to claim 1 wherein the casein glycomacropeptide is a kappa-caseino glycopeptide and a desialylated derivative thereof.

3. The method of claim 1 wherein the composition contains about 5 to about 10% by weight xylitol and 10 to about 20% by weight casein glycomacropeptide.

4. The method of claim 1 wherein the composition contains about 7 to about 10% by weight xylitol and about 10 to about 20% by weight of the casein glycomacropeptide.

* * * * *